United States Patent
Rautiainen et al.

(10) Patent No.: US 7,147,754 B2
(45) Date of Patent: Dec. 12, 2006

(54) SYSTEM FOR KEEPING CALENDER ROLLS OF A PAPER MACHINE CLEAN

(75) Inventors: Pentti Rautiainen, Järvenpää (FI); Harri Kuosa, Järvenpää (FI); Markku Kyytsönen, Numminen (FI)

(73) Assignee: Metso Paper, Inc., Helsinki (FI)

( * ) Notice: Subject to any disclaimer, the term of this patent is extended or adjusted under 35 U.S.C. 154(b) by 497 days.

(21) Appl. No.: 10/204,529

(22) PCT Filed: Feb. 21, 2001

(86) PCT No.: PCT/FI01/00175
§ 371 (c)(1),
(2), (4) Date: Nov. 20, 2002

(87) PCT Pub. No.: WO01/63048
PCT Pub. Date: Aug. 30, 2001

(65) Prior Publication Data
US 2003/0136538 A1 Jul. 24, 2003

(30) Foreign Application Priority Data
Feb. 24, 2000 (FI) .................................. 20000430

(51) Int. Cl.
*D21F 13/00* (2006.01)
(52) U.S. Cl. .................. 162/198; 162/199; 162/263; 162/272; 162/252; 34/117; 34/444; 34/445; 34/446; 427/316

(58) Field of Classification Search ................ 162/198, 162/199, 263, 272, DIG. 6, 252, 205; 34/117, 34/444–451; 427/316, 209
See application file for complete search history.

(56) References Cited

U.S. PATENT DOCUMENTS

| 5,848,452 A | * | 12/1998 | Lappalainen et al. ..... 15/256.51 |
| 6,413,371 B1 | * | 7/2002 | Ahonen et al. ............. 162/136 |
| 6,569,288 B1 | * | 5/2003 | Linnonmaa et al. ........ 162/207 |
| 6,584,703 B1 | * | 7/2003 | Maenpaa et al. ............. 34/446 |

FOREIGN PATENT DOCUMENTS

CA 2 227 541 A1 1/2000

(Continued)

OTHER PUBLICATIONS

Search Report issued in Finnish Priority Application No. 20000430.

(Continued)

*Primary Examiner*—Mark Halpern
(74) *Attorney, Agent, or Firm*—Stiennon & Stiennon

(57) ABSTRACT

A system for maintaining calender rolls of a paper machine clean when producing high-gloss paper or coated paper, such as LWC or MWC. To prevent a coating agent, such as coating dye, from adhering onto and soiling a smooth surface of a calender roll, with an overheating phenomenon, the system has a second measurement station (10) provided with measuring and indicator means for producing an output indicating soiledness of the web (W) or a humidity profile. When the output of the second measurement station (10) indicates excessive soiledness or an uneven humidity profile, the system performs at least one of: cleaning the surface of the smooth-surfaced calender roll; changing the nip load in the calender (5); making a correction adjustment of the CD-directional humidity profile of the web (W); cutting the web (W) and conducting it into the pulper; and/or changing the running speed of the web (W).

23 Claims, 2 Drawing Sheets

FOREIGN PATENT DOCUMENTS

Figure 1:
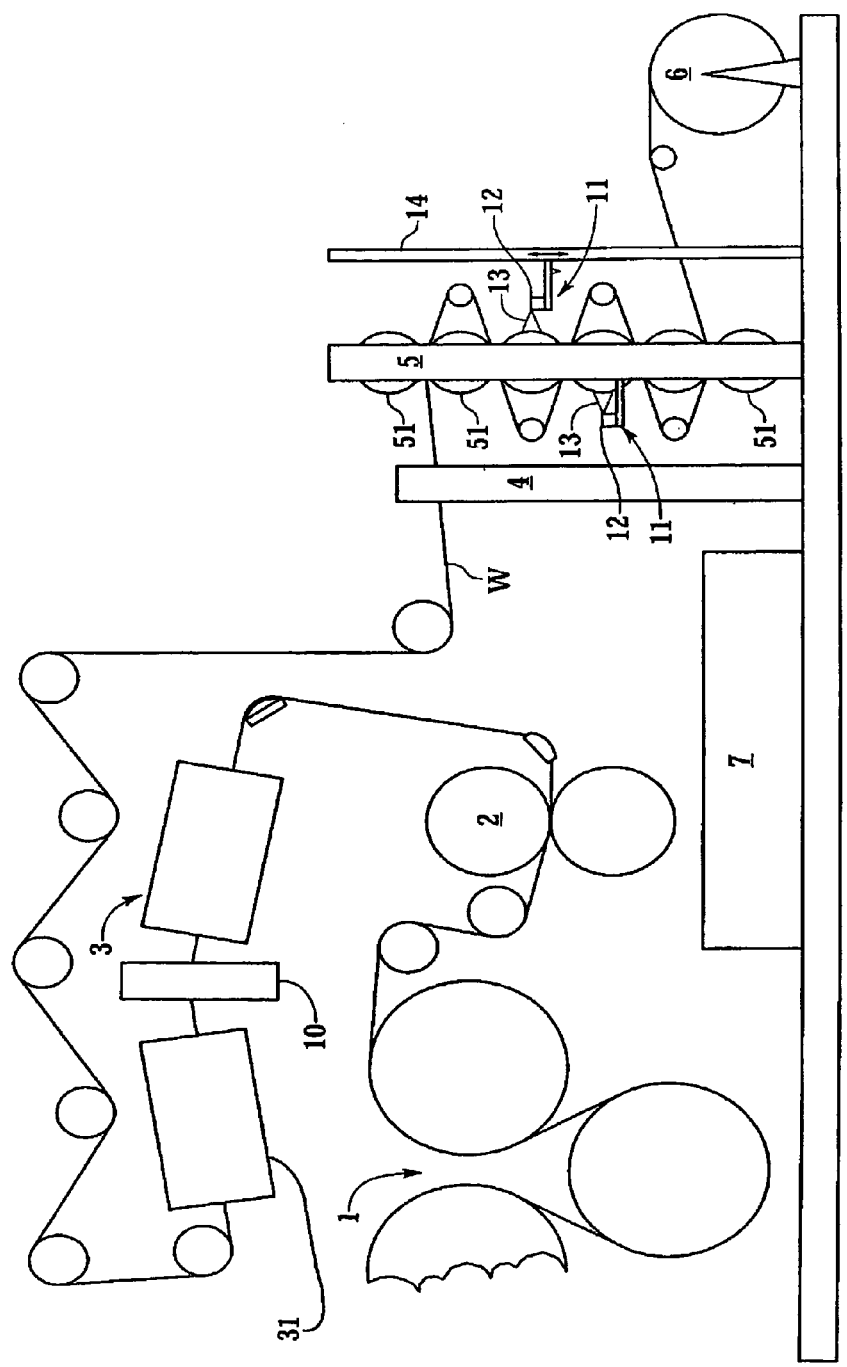

| | | |
|---|---|---|
| EP | 0 654 560 A2 | 5/1995 |
| EP | 0 972 882 A1 | 9/2000 |
| FI | 96895 | 5/1996 |
| WO | WO 99/67462 | 12/1999 |
| WO | WO 01/63048 | 8/2001 |

OTHER PUBLICATIONS

International Search Report issued in International Patent Application No. PCT/FI01/00175, Aug. 2002.

* cited by examiner

SYSTEM FOR KEEPING CALENDER ROLLS OF A PAPER MACHINE CLEAN

The present invention concerns a system for keeping calender rolls of a paper machine clean, including in a running direction, that is in the MD direction, of the web after a dryer section, a coating station, an additional dryer section and an On-Line calender prior to a reelin, unit, in producing high-gloss paper or coated paper.

It is known in the art to combine the Off-Line coating either with the Off-Line or On-Line calender, preferably with a multiple-nip calender for producing high-gloss paper or coated paper, such as LWC or MWC. Hereby, the problem is, in addition to intermediate reeling of the web, that the wet spots and streaks of the coating become caught on the calender rolls, resulting in local hot spots in the smooth surface of the calender rolls, leading to a greater deformation and uneven heating of the smooth surface of the calender roll, and hence, to a self-induced local overheating of the smooth surface of the calender. The end result of the overheating is fatal because the ordinary material of a roll coating is poorly heat conductive.

The objective of the present invention is to provide a novel method and a system for producing high-gloss or coated paper, such as LWC or MWC for the ON-Line calender, wherewith problems related to the prior art technology caused by soiling of the smooth surface and local overheating of the calender rolls could be eliminated or at least reduced.

This aim is achieved by the method and the system described above, wherewith the characteristic unique special features are mentioned in the accompanying claim assembly.

Therefore, the present invention is based on the novel and inventive basic insight that in order to prevent the coating agent, such as a coating dye and impurities of additives, from addhering onto the smooth surface of the calender roll and, as a result, the smooth surface of the calender roll from being soiled, and to prevent the overheating phenomenon and an extra heat exchange resistance of the thermoroll, the system includes another measurement station provided with measuring and indicator means for producing an output indicating the soiledness or the humidity profile of the web. When an output of the second measurement station indicates excessive soiledness or an uneven humidity profile, the system performs, as a response to the output of the second measurement station, at least one of the functions: cleaning of the surface of the smooth-surfaced calender roll; change of nip load in the calender; opening of nips; correction adjustment of the CD-direction humidity profile of the web; web cutting and conducting it into a pulper, and/or a change in the running direction of the web.

About the advantages of the invention, it is worthwhile to mention that the production loss is minimized by the invention being caused by cleaning and replacement operations of calender rolls and the intermediate reeling operations of the coated web.

Figure 2:
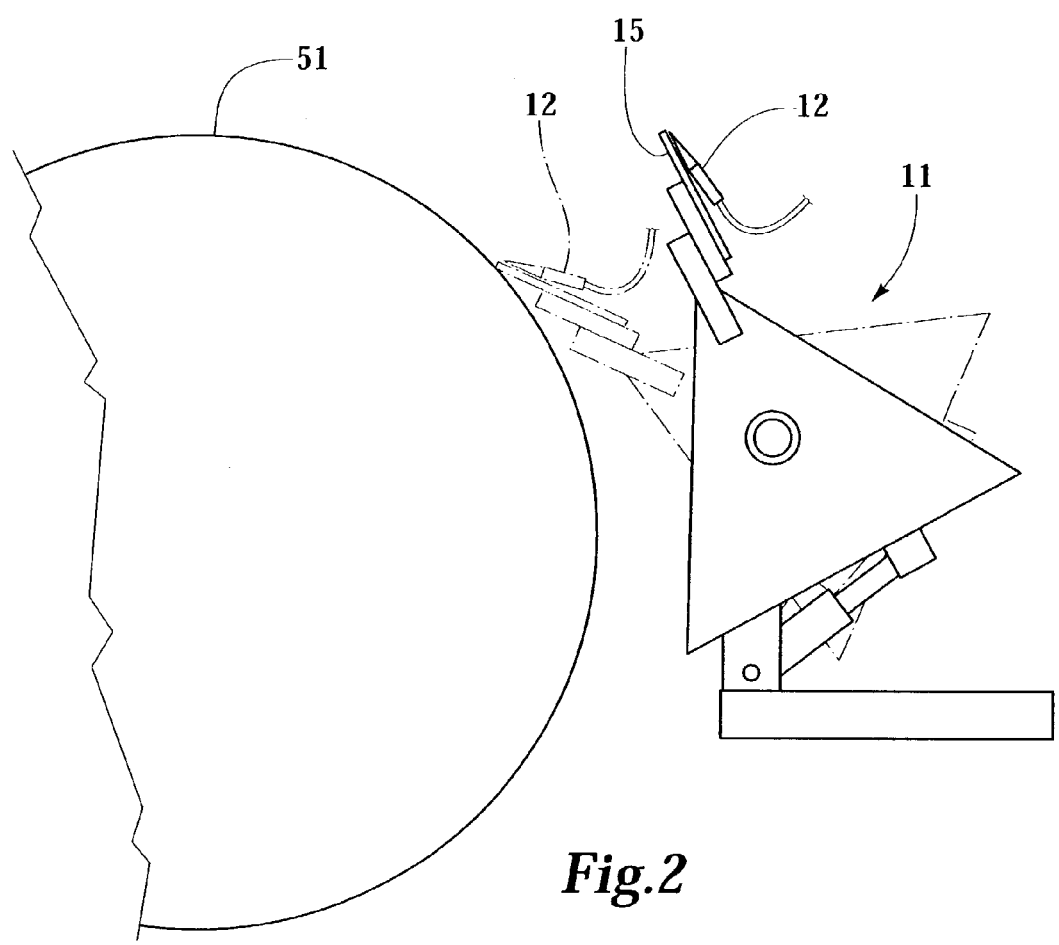

The invention is described below more in detail with the aid of an embodiment considered advantageous, reference being made to the accompanying drawing in which FIG. 1 presents schematically part of a paper machine including the system of the invention, and FIG. 2 presents schematically a cleaning unit of the invention.

The part of the machine demonstrated in the drawing includes, in the running direction of the web W, that is in MD direction, arranged after the dryer section 1 a coating station 2, an additional dryer section 3, a measurement station 4 and a calender 5, which is advantageously a multiple-nip On-Line calender, positioned before the reeling unit 6.

The aim of the present in vention is to prevent the coating dye from addhering onto the smooth surface of the calender roll and, as a result, to prevent the smooth surface of the calender roll from becoming soiled and to prevent the overheating phenomenon. To achieve said aim, the system includes a second measurement station 10, provided with measuring and indicator means to produce an output indicating the soiledness or the transverse direction, that is CD direction, humidity profile of the web W. When an output of the second measurement station 10 indicates excessive soiledness or an uneven humidity profile in the web W, the system performs, on an impulse of the output, one or more of the following functions to prevent the smooth-surfaced calender roll from becoming soiled: cleaning of the surface of the smooth-surfaced calender roll 51, change in nip load in the calender 5, correction adjustment of the CD direction humidity profile of the web W; cutting of the web W and guiding it into the pulper 7, and/or a change of the running speed of the web W.

In the CCC (Coated Calender Control) system of the present invention the essential aspect is that after the last coating station the web is continously measured in the above-mentioned second measurement station 10, being in the running or MD direction to the web W positioned after the coating station 2. Hereby, on the basis of an output of the second measurement station 10, wet streaks and spots in the web can be detected, which will cause e.g. holes in the web W. Wet streaks and spots may also be caused by e.g. disturbances in the coating station 2, this in turn being caused by e.g a fixed particle entrapped between the measuring unit (not shown in the drawing) before the coating station and the web.

In the advantageous embodiment of the invention, the humidity of the web is measured by continuous point measurement, whereby disturbances in the dryer units and/or the coating station are detected, causing either inadequate drying of the web in the dryer apparatus or excessive spreading of the coating mixture from the spreading unit.

In addition and in parallel to measuring the humidity profile or soiledness of the web W, it is advantageous to provide a correction adjustment of the CD direction humidity profile of the web in the last drying group 31 of the additional dryer section 3, said operation being, according to the invention, preferably implemented using infrared heaters. Said correction adjustment is preferably implemented by means of zone-controlled dryer units in the last drying group for correcting the CD-direction humidity profile of the web without any risk of overdrying the sufficiently dried web.

In the system of the invention, soiling of calender rolls can be reduced further and therethrough the calender rolls can be protected by reducing the nip load of the calender 5 when the humidity of the web W exceeds a permitted limit while being still sufficiently low for drawing the web W through a substantially unloaded calender nip/nips. In addition, it is particularly of importance, according to the invention, to prevent the calender rolls from becoming soiled that the calender nip is opened when, on the basis of an output of the second measurement station 10, the local humidity content of the humidity profile of the web W exceeds a predetermined limit and when to a limited extent, wet spots of the coating agent, being apt to catch on, are detected on the web W.

It is furthermore essential, considering the soiling of calender rolls, particularly when, on the basis of an output of the second measurement station 10, the local humidity content of the humidity profile or the soiledness of the web W, resulting in a disturbance in the coating process, exceeds a predetermined limit value that the web W is cut before the calender 5 and conducted into the pulper 7.

When the web W is conducted into the pulper 7, it is important, considering the minimization of broke, that the running speed of the web W in the coating station 2 is decelerated.

After the humidity profile or the humidity of the web W is on an acceptable level after the coating station adjustments, the tail of the web W is again threaded through the calender 5, whereafter the running speed of the web W in the coating station 2 and in the calender 5 is accelerated back to the production speed.

FIG. 2 presents as a schematic diagram a cleaning unit 11 of the invention, intended for cleaning a smooth-surfaced calender roll, which is positioned, as being an essential feature in the invention, to be moved away, said position being demonstrated by an intact line in FIG. 2, and towards the calender roll to be cleaned, which position is demonstrated by a broken line in FIG. 2. In this case, it is advantageous, according to the invention that the cleaning unit is disposed to be either fixedly in the calender 5, e.g with the aid of a fixed support arm in the support frame of the calender rolls to be in connection with each calender roll with smooth surface or to be movable/transferrable in connection with the calender roll with a smooth surface, When the cleaning unit is a movable/transferrable cleaning unit 11, it is advantageously positioned to be supported by vertical guides in a portal support 14, so that the cleaning unit 11 can be moved to be in the adjacency of a calender roll requiring cleaning.

As taught by the invention, the cleaning unit 11 is provided with a means 12 for generating a pressurized jet. Advantageously, said means is a pressure washer 12, the jet/jets of which and focussing of the jet/jets of which in CD direction towards the surface of the calender roll is controlled by an output of the second measurement station. It is advantageous, in addition to the pressurized jet, that the cleaning unit is also provided with a doctor blade 15 which blade moves most advantageously together with the cleaning unit 11 on and off the surface of the calender roll, which in this manner aids in cleaning the smooth-surfaced calender roll.

The invention is described in the preceding merely in exemplary fashion with the aid of an embodiment considered to be advantageous It goes without saying that the invention is not desired to be confined therewith; instead, a plurality of other alternative solutions and modifications, especially concerning the composition of the production line of paper, etc. and embodying of the present invention therein, are conceivable within the protective scope of the inventive idea as determined in the accompanying claims.

The invention claimed is:

1. A system for maintaining calender rolls of a paper machine clean when producing high-gloss paper or coated paper, the system comprising:
   a dryer section;
   a coating station;
   an additional dryer section;
   a first measuring station;
   a multi-nip on-line calender having a plurality of calender rolls;
   a reeling unit,
   a web passing from the dryer section to the coating station to the additional dryer section, to the first measuring station, to the calender, and then to the reeling unit;
   a second measurement station positioned to receive the web after the coating station but before the calender, which is provided with measuring and indicator means for producing an output indicating the soiledness of the web or a humidity profile in a CD direction, the second measurement station arranged to output an indicator of excessive soiledness or uneven humidity profile;
   an apparatus responsive to an output of the second measurement station indicative of excessive soiledness, or uneven humidity profile said apparatus having a configuration and structure sufficient to perform at least one function selected from a group consisting of:
   cleaning of the surface of the smooth-surfaced calender roll;
   changing the nip load in the calender;
   making a correction adjustment of the CD-directional humidity profile of the web;
   cutting the web and conducting it into a pulper; and
   changing the running speed of the web.

2. The system of claim 1, wherein the calender of the system has a plurality of smooth-surfaced calender rolls, and a cleaning unit positioned for the cleaning of the smooth-surfaced calender rolls which is arranged to be either fixedly in connection with the smooth-surfaced calender rolls or moveable/transferrable into connection with the smooth-surfaced calender roll.

3. The system of claim 2, wherein the cleaning unit comprises a pressurized jet directed toward the smooth-surfaced calender roll.

4. The system of claim 2, wherein the cleaning unit further comprises a doctor blade being movable off and against the smooth-surfaced calender roll.

5. The system of claim 1, wherein the second measurement station is positioned so the web extends to a dryer section after the second measurement station.

6. The system of claim 1, wherein the additional dryer section is made of infrared heaters.

7. The system of claim 1, wherein in order to protect the calender rolls, the system further comprises apparatus which reduces the nip load of the calender when the local humidity of the humidity profile of the web indicated by the output of the second measurement station exceeds a permitted limit value while being still low enough to take the web through the substantially unloaded calender nip/nips.

8. The system of claim 1, wherein the calender nip opens when the output of the second measurement station indicates spots of wet coating agent in the web and when the local humidity content of the humidity profile of the web exceeds a predetermined limit.

9. The system of claim 8, further comprising apparatus which when the web is conducted into the pulper, reduces the running speed of the web in the coating station to minimize broke.

10. The system of claim 8, further comprising apparatus which after the humidity profile or the humidity of the web is on an acceptable level after the coating station adjustments, again threads the tail of the web through the calender, and which thereafter accelerates the running speed of the web in the coating station and in the calender back to a production speed.

11. The system of claim 1, further comprising apparatus which, when the output of the second measurement station indicates a humidity content in the humidity profile of the web which as a result of a disturbance of the coating process exceeds a predetermined limit value, cuts the web prior to the calender and conducts it into the pulper.

12. A method for maintaining calender rolls of a paper machine clean when producing high-gloss paper or coated paper, the method comprising the steps of:
drying a paper web in a dryer section;
coating the paper web in a coating station;
drying the paper web in an additional dryer section;
measuring the paper web in a first measuring station;
calendering the web in a multi-nip on-line calender having a plurality of calender rolls;
reeling the paper web in a reeling unit, and passing the paper web from the dryer section to the coating station to the additional dryer section, to the first measuring station, to the calender, and then to the reeling unit;
measuring the paper web in a second measurement station with measuring and indicator means and producing an output indicating the soiledness of the web or a humidity profile in a transverse CD direction;
preventing coating dye from adhering onto a smooth surface of a calender roll and thus preventing the smooth surface of said calender roll from becoming soiled and thus also preventing an overheating phenomenon and an extra heat-transfer resistance of a thermoroll by detecting an output of the second measurement station which indicates excessive soiledness or uneven humidity profile and in response to said detected output performing at least one function selected from the group consisting of:
cleaning the surface of a smooth-surfaced calender roll of the calender;
changing the nip load in the calender;
making a correction adjustment of the CD-directional humidity profile of the web;
cutting the web and conducting it into a pulper; and
changing the running speed of the web.

13. The method of claim 12 wherein the at least one function selected from the group is cleaning the surface of the smooth-surfaced calender roll of the calender.

14. The method of claim 12 wherein the at least one function selected from the group is changing the nip load in the calender.

15. The method of claim 12 wherein the at least one function selected from the group is making a correction adjustment of the CD-directional humidity profile of the web.

16. The method of claim 12 wherein the at least one function selected from the group is cutting the web and conducting it into a pulper.

17. The method of claim 12 wherein the at least one function selected from the group is changing the running speed of the web.

18. A method for maintaining calender rolls of a paper machine clean when producing coated paper, the method comprising:
drying a paper web in a dryer section;
coating the paper web in a coating station, to form a coated web;
further drying the coated web in an additional dryer section;
measuring in a first measuring station a parameter of the coated web before a last dryer group of the additional dryer section;
measuring in a second measuring station a parameter of the coated web indicating excessive soiledness or an uneven humidity profile in the web, the measuring taking place before a multi-nip on-line calender having a plurality of calender rolls, and in response to said detected output, preventing coating dye from adhering onto a smooth surface of a calender roll by performing at least one function selected from the group consisting of:
cleaning the surface of a smooth-surfaced calender roll of the plurality of calender rolls of the calender;
changing the nip load in the calender;
making a correction adjustment of the CD-directional humidity profile of the web;
cutting the web and conducting it into a pulper; and
changing the running speed of the web; and
further comprising the step of: when the paper passes through the calender winding it on a reel following the calender.

19. The method of claim 18 wherein the step performed responsive to the output of the second measurement station is cleaning of the surface of the smooth-surfaced calender roll.

20. The method of claim 18 wherein the step performed responsive to the output of the second measurement station is changing the nip load in the calender.

21. The method of claim 18 wherein the step performed responsive to the output of the second measurement station is making a correction adjustment of the CD-directional humidity profile of the web.

22. The method of claim 18 wherein the step performed responsive to the output of the second measurement station is cutting the web and conducting it into a pulper.

23. The method of claim 18 wherein the step performed responsive to the output of the second measurement station is changing the running speed of the web.

* * * * *

UNITED STATES PATENT AND TRADEMARK OFFICE
CERTIFICATE OF CORRECTION

PATENT NO. : 7,147,754 B2 Page 1 of 1
APPLICATION NO. : 10/204529
DATED : December 12, 2006
INVENTOR(S) : Pentti Rautiainen et al.

It is certified that error appears in the above-identified patent and that said Letters Patent is hereby corrected as shown below:

In column 1, below the Title insert --CROSS REFERENCES TO RELATED APPLICATIONS This Application is a U.S. national stage application of International Application No. PCT/FI01/00175, filed Feb. 21, 2001, and claims priority on Finish Application No. 20000430 filed Feb. 24, 2000, the disclosures of both these applications being hereby incorporated by reference herein.--

In column 1, line 8, "reelin, unit," should be --reeling unit,--

In column1, line 25, "ON-Line" should be --On-Line--

In column 1, lines 30-32, delete the sentence "This aim is achieved by the method and the system described above, wherewith the characteristic unique special features are mentioned in the accompanying claim assembly."

In column 1, line 36, "addhering" should be --adhering--

In column 1, line 46, "the functions" should be --the following functions--

In column 2, line 3, after "adventageous" insert a period

Signed and Sealed this

Sixth Day of March, 2007

JON W. DUDAS
*Director of the United States Patent and Trademark Office*